US00PP27158P3

(12) United States Plant Patent
Warren et al.

(10) Patent No.: US PP27,158 P3
(45) Date of Patent: Sep. 13, 2016

(54) CALLA LILY PLANT NAMED 'CARDINAL BLZ'

(50) Latin Name: ***Zantedeschia* spp.**
Varietal Denomination: Cardinal BLZ

(71) Applicants: Andrew Geoffrey Fiennes Warren, Tauranga (NZ); Jacobus P. Spaans, Oudorp (NL)

(72) Inventors: Andrew Geoffrey Fiennes Warren, Tauranga (NZ); Jacobus P. Spaans, Oudorp (NL)

( * ) Notice: Subject to any disclaimer, the term of this patent is extended or adjusted under 35 U.S.C. 154(b) by 187 days.

(21) Appl. No.: 14/121,667

(22) Filed: Oct. 6, 2014

(65) Prior Publication Data
US 2016/0100515 P1 Apr. 7, 2016

(51) Int. Cl.
*A01H 5/02* (2006.01)

(52) U.S. Cl.
USPC ..... Plt./490

(58) Field of Classification Search
USPC ..... Plt./490
CPC ..... A01H 5/02
See application file for complete search history.

*Primary Examiner* — Kent L Bell

(57) ABSTRACT

A calla lily plant particularly distinguished by red spathes, light-medium maculation of the leaves that is visible from both sides and producing 4 to 6 inflorescences per 3-cm tuber is described.

3 Drawing Sheets

Genus and species: *Zantedeschia* spp.
Variety denomination: 'Cardinal BLZ'.

BACKGROUND OF THE NEW PLANT

The present invention comprises a new and distinct cultivar of calla lily, botanically known as *Zantedeschia* spp., and hereinafter referred to by the cultivar name 'Cardinal BLZ'. The new cultivar was asexually reproduced by tissue culture resulting from the cross of the female parent an unnamed, unpatented *Zantedeschia* variety having red-pink spathes and the male parent an unnamed, unpatented *Zantedeschia* variety having red spathes. 'Cardinal BLZ' is a product of a planned breeding program intended to create new calla lily plants with red spathes.

The new cultivar was created in Tauranga, New Zealand and has been asexually reproduced repeatedly by tissue culture in Bangalore, India over a two year period. The present invention has been found to retain its distinctive characteristics through successive propagations.

'Cardinal BLZ' has not been made publicly available anywhere in the world more than one year prior to the filing date of this application.

SUMMARY OF THE INVENTION

The following are the most outstanding and distinguishing characteristics of this new cultivar when grown under normal horticultural practices in Tauranga, New Zealand.

1. Red spathes
2. Light to medium maculation of the leaves that is visible from both sides; and
3. Produces 4 to 6 inflorescences per 3-cm tuber.

DESCRIPTION OF THE PHOTOGRAPHS

This new calla lily plant is illustrated by the accompanying photographs which show the plant habit, mature inflorescence and foliage of the plant. The colors shown are as true as can be reasonably obtained by conventional photographic procedures. The photographs are of a plant approximately 8 weeks old, after planting in optimum conditions.

Figure 1:
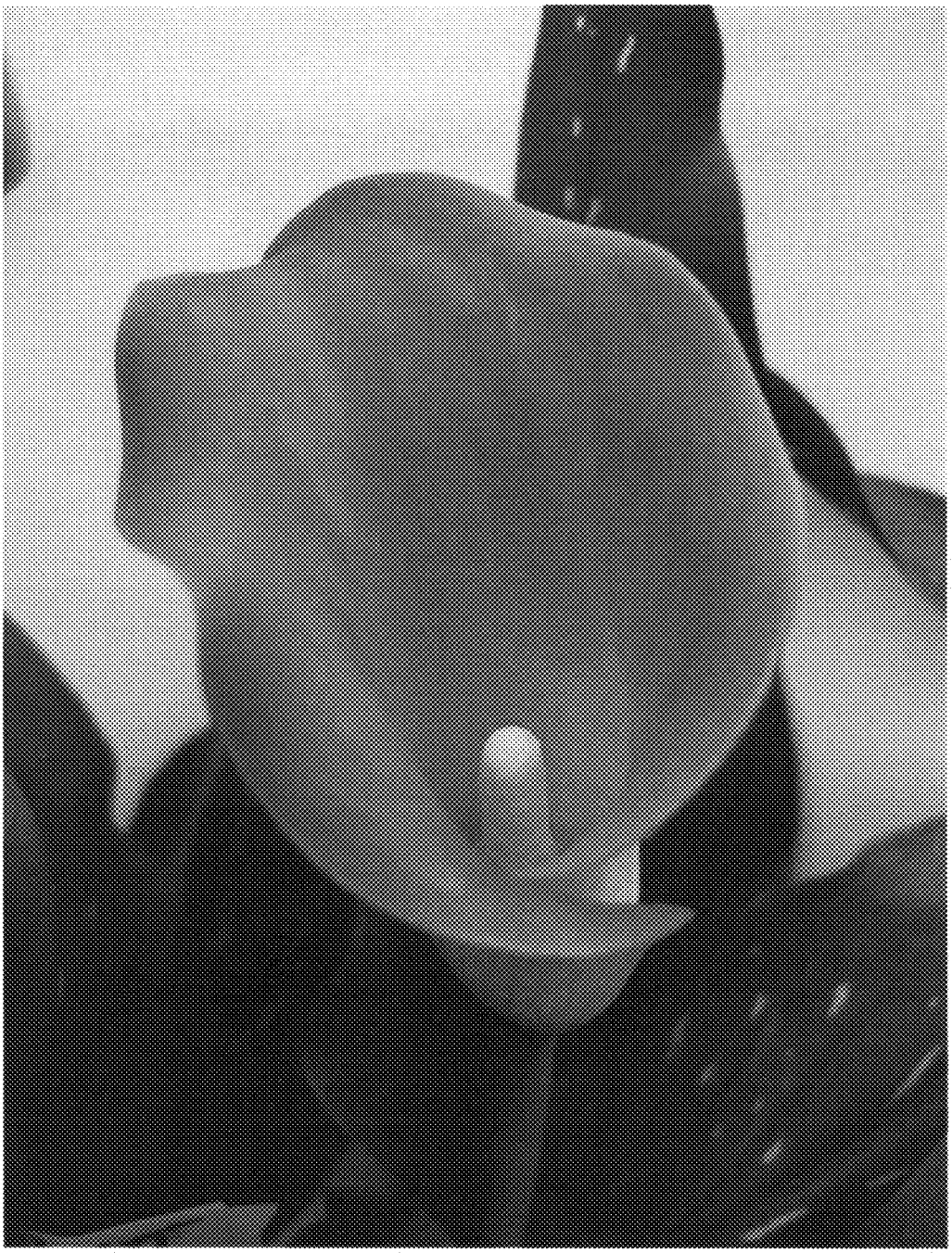
Figure 2:
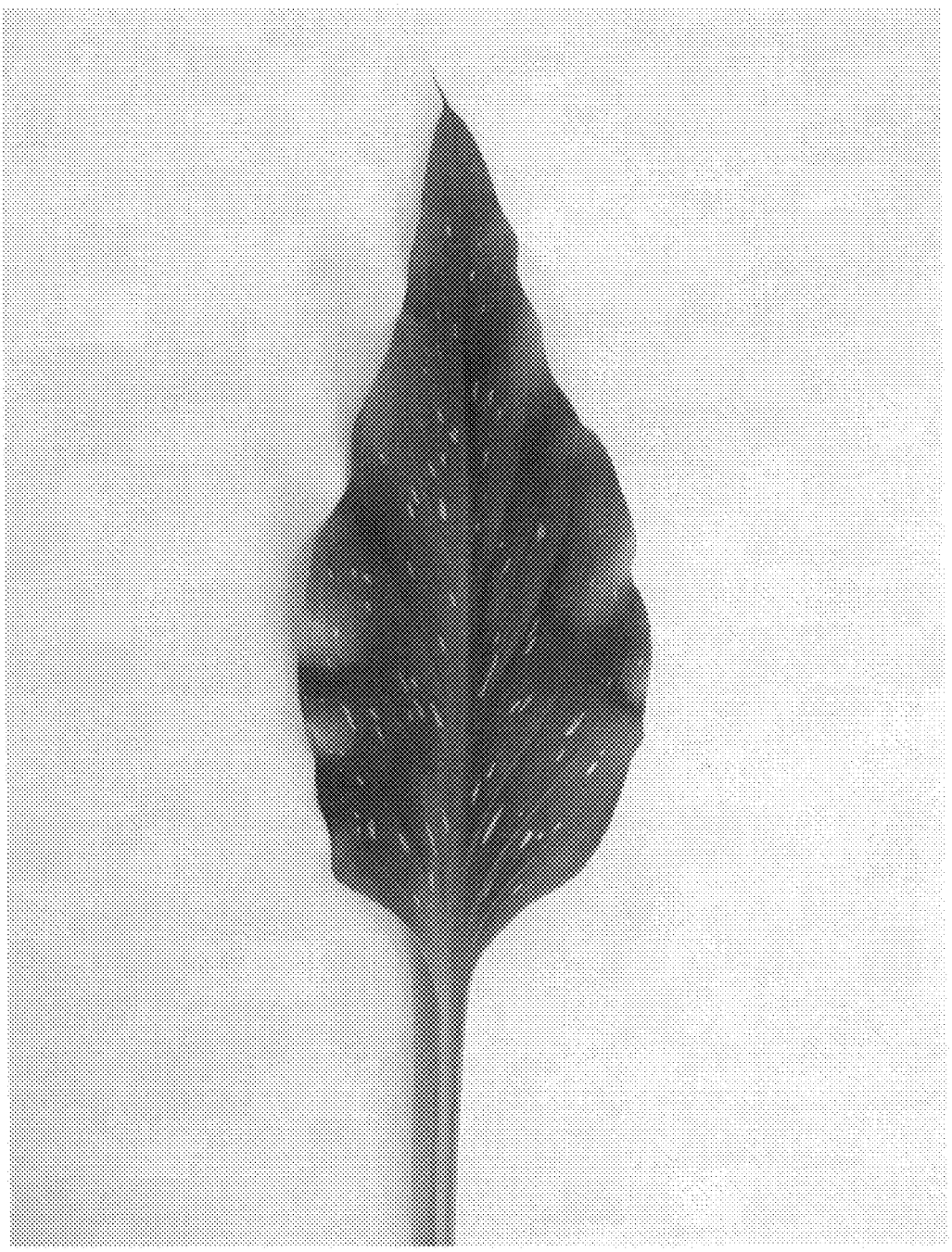
Figure 3:
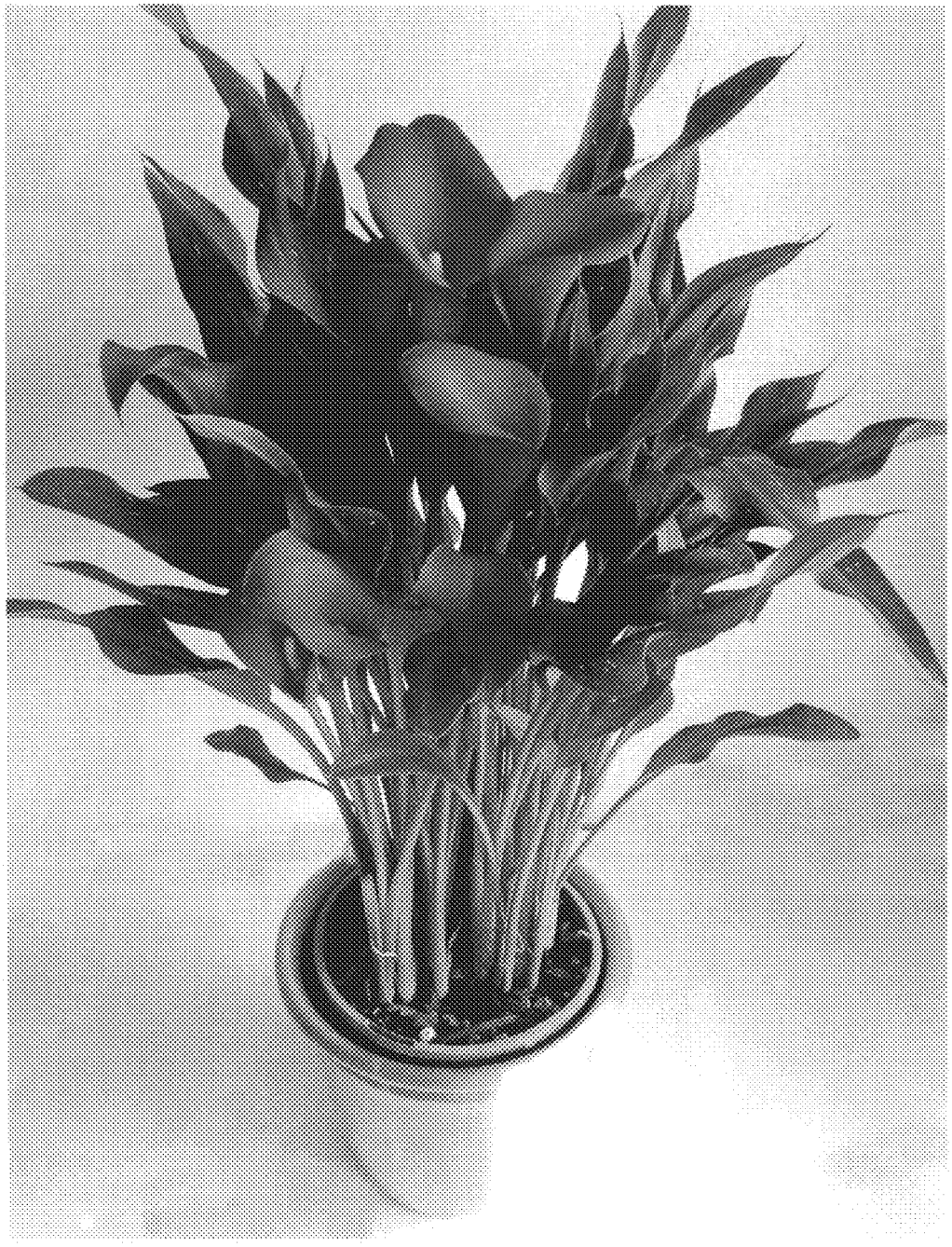

FIG. 1 shows a close-up of a mature inflorescence.
FIG. 2 shows a close-up of the leaf.
FIG. 3 shows the mature inflorescence and foliage.

DESCRIPTION OF THE NEW CULTIVAR

The following detailed description sets forth the distinctive characteristics of 'Cardinal BLZ'. The data that define these characteristics were collected from asexual reproductions carried out in New Zealand. The plant history was taken on plants of two-year-old tubers based on a 3-cm diameter tuber under New Zealand summer conditions. Color references are primarily to the 1995 edition of The Colour Chart of The Royal Horticultural Society of London (R.H.S.).

DETAILED BOTANICAL DESCRIPTION

Classification:
- *Family.*—Araceae.
- *Botanical name.*—*Zantedeschia* spp.
- *Common name.*—Calla lily.

Parentage:
- *Female parent.*—An unnamed, unpatented *Zantedeschia* variety having pink-red spathes.
- *Male parent.*—An unnamed, unpatented *Zantedeschia* variety having red spathes.

Plant:
- *Form.*—Erect.
- *Height of the leaf canopy above the soil.*—35 cm to 50 cm.
- *Height of top of inflorescence above the soil.*—20 cm to 40 cm.
- *Diameter.*—35 cm to 45 cm.

*Number of inflorescences per tuber size.*—Tuber diameter 3 cm: 4 to 6. Tuber diameter 4 cm: 6 to 12. Tuber diameter 5 cm: 10+.

*Time to produce a finished flowering plant.*—6 to 8 weeks depending on the climate and environment.

*Lastingness of the inflorescence on the plant.*—2 to 4 weeks.

Growing points:

*Character.*—Strong.

*Color.*—Upper: RHS 144A. Lower: RHS 144B. Base: RHS 144B.

*Average number.*—6 to 10.

Leaves:

*Size.*—Length: 15 cm to 20 cm. Width: 5 cm to 8 cm.

*Shape.*—Ovate.

*Apex.*—Apiculate.

*Base.*—Attenuate.

*Margin.*—Undulate.

*Margin color.*—RHS 146B (yellow-green).

*Venation pattern.*—Pinnate.

*Surface texture.*—Leathery.

*Color.*—Upper surface: RHS 137C (green). Lower surface: RHS 137D (green).

*Maculation* (*leaf spots*).—General: Maculation is only on the upper surface of the leaf but is visible from the lower surface. Density: Light to medium density. Color: RHS 155B (white).

*Petiole.*—Average number per tuber: 15 to 20. Length: 22 cm to 30 cm. Diameter: 0.4 cm to 0.6 cm. Texture: Smooth. Character: Strong. Shape: Slightly flattened with shallow ridge on adaxial surface. Color: Base: RHS 144B (yellow-green), mottled with white. Upper portion: RHS 144B (yellow-green). Sheath: Length: 5 cm to 7 cm. Diameter: 0.6 cm to 0.8 cm. Color: RHS 144B (yellow-green).

Roots:

*Color.*—RHS 155D (white).

*Branching.*—Not branched, attached to the top of the tuber at the apices.

Inflorescence:

*Spathe* (*flower body*).—Size: Length: 5.5 cm to 7 cm. Width: 4.0 cm to 5.5 cm. Height: 4.5 cm to 6 cm. Color: Upper portion: RHS 53C (red). Lower portion: RHS 53C (red). Outer surface of the base: some yellow coloration RHS 8D. Fading: darkens to RHS 53B (red) on the inner surface and RHS 53A (red-purple) on the outer surface. Vein color: RHS 53C (red). Fragrance: Absent. Shape: Round. Texture: Smooth. Apex: Apiculate. Base: Attenuate. Margin: Slightly undulate. Size of throat spot: absent.

*Spadix* (*reproductive organs*).—Size: Length: 2.5 cm to 4 cm. Diameter: 0.5 cm to 0.7 cm. Color: Base: RHS 53A (red). Upper part: RHS 14B (yellow-orange). Position relative to spathe: Upright. Shape: Elongated. Apex: Rounded.

*Peduncle* (*flower stem*).—Length: 20 cm to 45 cm. Diameter: 0.3 cm to 0.45 cm. Color: Base: RHS 144B (yellow-green). Upper part: RHS 144B (yellow-green). Surface texture: Smooth. Strength: Moderate.

Reproductive organs:

*Location of female organs.*—Basal position of the spadix.

*Location of male organs.*—Upper position of the spadix.

*Perianth* (*the floral envelope, calyx and corolla*).—Conspicuous.

*Pollen color.*—RHS 155D (white).

*Stamens.*—Not visible before pollen release.

*Pistil.*—Number: 25 to 30 per spadix. Color: RHS 14A (yellow-orange).

Fruit (berries):

*Quantity of berries per plant.*—25 to 30.

*Color.*—RHS 143B.

*Size.*—Length: 3.5 cm to 4.5 cm (whole fruit). Width: 2.5 cm to 3 cm (whole fruit). Diameter: 0.5 cm to 0.8 cm (individual berry).

Disease and insect resistance:

*Disease resistance.*—No susceptibility to date.

*Pest resistance.*—No susceptibility to date.

COMPARISON WITH PARENTAL AND KNOWN CULTIVARS

When compared to the commercial variety 'Merlot BLZ' (U.S. Plant Pat. No. 19,867), 'Cardinal BLZ' has narrower, lighter coloured leaves and red spathe colour.

When compared to the commercial variety 'Majestic Red', 'Cardinal BLZ' has narrower leaves, a larger number and more uniform inflorescences and red spathe colour.

When compared to the female parent, 'Cardinal BLZ' has wider leaves, a greater number of inflorescences and a more rounded flower spathe.

When compared to the male parent 'Cardinal BLZ' has a less dense leaf maculation pattern, a greater number of inflorescences and red spathe colour.

I claim:

1. A new and distinct cultivar of calla lily plant as shown and described herein.

* * * * *